(12) United States Patent
Kroselj et al.

(10) Patent No.: US 8,921,352 B2
(45) Date of Patent: Dec. 30, 2014

(54) PHARMACEUTICAL COMPOSITION COMPRISING SIMVASTATIN AND EZETIMIBE

(75) Inventors: Vesna Kroselj, Sentjernej (SI); Renata Lakse, Smarjeske Toplice (SI); Rebeka Toporisic, Brezice (SI); Joze Kastelic, Krka (SI)

(73) Assignee: KRKA, Novo Mesto (SI)

( * ) Notice: Subject to any disclaimer, the term of this patent is extended or adjusted under 35 U.S.C. 154(b) by 976 days.

(21) Appl. No.: 11/994,782

(22) PCT Filed: Jun. 30, 2006

(86) PCT No.: PCT/EP2006/006369
§ 371 (c)(1),
(2), (4) Date: Aug. 6, 2008

(87) PCT Pub. No.: WO2007/000365
PCT Pub. Date: Jan. 11, 2007

(65) Prior Publication Data
US 2008/0300233 A1 Dec. 4, 2008

(30) Foreign Application Priority Data
Jul. 6, 2005 (EP) ..................................... 05014680

(51) Int. Cl.
*A61K 31/397* (2006.01)
*A61P 9/10* (2006.01)
*A61K 9/20* (2006.01)
*A61K 9/28* (2006.01)
*A61K 31/366* (2006.01)

(52) U.S. Cl.
CPC ............. *A61K 31/397* (2013.01); *A61K 9/2018* (2013.01); *A61K 9/2866* (2013.01); *A61K 31/366* (2013.01); *A61K 9/2054* (2013.01); *A61K 9/284* (2013.01)
USPC .................................................... 514/210.02

(58) Field of Classification Search
USPC .................................................... 514/210.02
See application file for complete search history.

(56) References Cited

U.S. PATENT DOCUMENTS

| 5,846,966 | A | 12/1998 | Rosenblum et al. |
| 6,235,311 | B1 * | 5/2001 | Ullah et al. ................... 424/472 |
| 7,030,106 | B2 * | 4/2006 | Cho ......................... 514/210.03 |
| 2002/0132359 | A1 | 9/2002 | Waterman |
| 2003/0068366 | A1 * | 4/2003 | Chungi et al. ................ 424/452 |
| 2006/0223882 | A1 * | 10/2006 | Sundaram et al. ............ 514/460 |

FOREIGN PATENT DOCUMENTS

| EP | 0033538 | 8/1981 |
| EP | 0299656 | 1/1989 |
| EP | 0351918 | 1/1990 |
| WO | 03/055467 | 7/2003 |
| WO | 2004010993 | 2/2004 |
| WO | 2004071402 | 8/2004 |
| WO | 2005009955 | 2/2005 |
| WO | 2005011638 | 2/2005 |

OTHER PUBLICATIONS

Coleman (Exetimibe/simvastatin, Formulary, vol. 39, Sep. 2004, pp. 437-444).*
"Vytorin", http://www.rxlist.com/cgi/generic3/vytorin.htm, [Online]; Aug. 12, 2004; 41 pages; XP002339697.
Waterman, K et al., "Stabilization of Pharmaceuticals to Oxidative Degradation," Pharmaceutical Development and Technology, vol. 7, No. 1, pp. 1-32, (2002).
Written Opinion of the International Searching Authority dated Jun. 30, 2006, 6 pgs.

* cited by examiner

*Primary Examiner* — San-Ming Hui
*Assistant Examiner* — Kathrien Cruz
(74) *Attorney, Agent, or Firm* — K&L Gates LLP

(57) ABSTRACT

The present invention relates to the field of pharmaceutical technology and in particular to novel dosage forms of medicaments containing as active ingredients simvastatin and ezetimibe, or pharmaceutically acceptable salts thereof. The present pharmaceutical compositions are characterized in that the contact of the compositions with oxygen is substantially reduced, such as by coating the composition, providing a medicament useful for the treatment and prevention of atherosclerosis and related conditions, in an environment having an essentially reduced oxygen or humidity, respectively, content.

12 Claims, No Drawings

PHARMACEUTICAL COMPOSITION COMPRISING SIMVASTATIN AND EZETIMIBE

The present invention relates to the field of pharmaceutical technology and in particular to novel dosage forms of medicaments containing as active ingredients simvastatin and ezetimibe, or pharmaceutically acceptable salts thereof. The pharmaceutical compositions are characterized in that no stabilizing agents, particularly antioxidants, are utilized therein and/or the contact of the compositions with oxygen is substantially reduced, such as by coating the composition or providing the medicament in an environment having an essentially reduced oxygen or humidity, respectively, content.

High blood or plasma cholesterol levels or hypercholesterolemia represent a common disease pattern preliminary in the well situated countries of the western hemisphere. Cholesterol may cause a "hardening of the arteries" so that arteries become narrowed and blood flow to the heart is slowed down or even blocked with the consequence that provision of oxygen to the organs is constrained. Hypercholesterolemia has been implicated in atherosclerosis, heart attack, and stroke and is one of several conditions that may lead to coronary artery disease, which is the leading cause of death in the United States, accounting for approximately 600,000 deaths per year. The risk group includes the overweight, smokers, those with a poor diet (e.g. one rich in saturated fats), those who take inadequate exercise and suffering from stress. For such risk individuals, as well as those tested and found to have unduly high plasma cholesterol levels, a variety of treatments have been proposed, e.g. changes in diet and habits, increased exercise, etc. However such treatments are not always easy to enforce and there exist also medicinal treatments which have been effective at reducing plasma cholesterol levels.

Commonly used compounds for the treatment or prevention of high cholesterol levels in individuals are the statins, such as fluvastatin, simvastatin, and lovastatin. Among the group of statins, particularly simvastatin exhibited good results in the treatment of conditions characterized by high cholesterol levels. Said compound has the following structure formula (I):

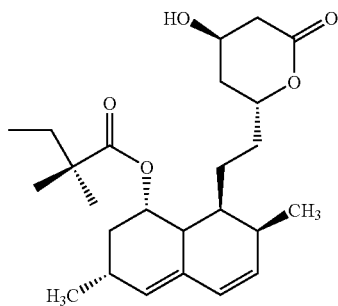

while methods for its preparation are disclosed in e.g. in EP 0 033 538, EP 0 351 918, and EP 0 299 656. Simvastatin exerts a cholesterol reducing effect by inhibiting the conversion of 3-hydroxy-3-methylglutaryl coenzyme A (HMG-CoA) to mevalonate, an early step in the biosynthetic pathway of cholesterol. Additionally, simvastatin reduces the amount of very-low density lipoproteins (VLDL) and triglycerides (TG) and increases high-density lipoprotein cholesterol (HDL-C) and is thus capable to counteract diseases like atherosclerosis. Simvastatin is marketed worldwide and sold under the trade name ZOCOR®. ZOCOR® tablets contain simvastatin, anhydrous lactose, microcrystalline cellulose (carriers), pregelatinized maize starch (disintegrant), magnesium stearate (lubricant), butylated hydroxyanisol (BHA), citric acid monohydrate and ascorbic acid (antioxidants).

Also other compounds having a different mode of action with regard to a reduction of blood cholesterol levels have been proposed for use. Ezetimibe, which is disclosed in EP 0 720 599 and identified by the structure formula (II):

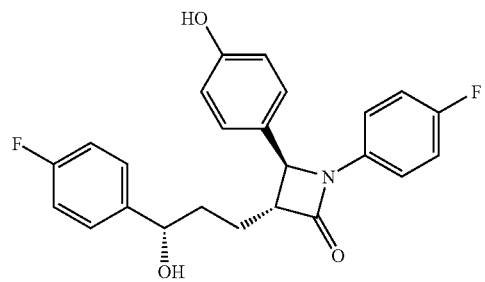 [SMILES: O=C1[C@H](CC[C@H](O)c2ccc(F)cc2)[C@@H](c2ccc(O)cc2)N1c1ccc(F)cc1]

is such a compound. The mechanism of absorption and resorption inhibition of cholesterol of ezetimibe involves increased excretions of cholesterol and its intestinally generated metabolites with the faeces. This effect results in lowered body cholesterol levels, increased cholesterol synthesis, and decreased triglyceride synthesis. The increased cholesterol synthesis initially provides for the maintenance of cholesterol levels in the circulation, levels that eventually decline as the inhibition of cholesterol absorption and resorption continues. The overall effect of drug action is the lowering of cholesterol levels in the circulation and tissues of the body. In the USA it is market under the trade name ZETIA®. Polymorphic forms of this ezetimibe are for example described in WO 2005/009955.

In order to provide improved medication the art considered combination products, such as e.g. a combination of ezetimibe and simvastatin, which is marketed for example in the USA under the trade name VYTORIN®. The commercially available VYTORIN® tablets contain ezetimibe, simvastatin, lactose monohydrate, microcrystalline cellulose (carriers), hydroxylpropyl methylcellulose (binder), croscarmellose sodium (disintegrant), magnesium stearate (lubricant), butylated hydroxyanisol (BHA), citric acid monohydrate and propyl gallate (antioxidants). For the time being, combinations comprising 10 mg of ezetimibe each and 10, 20, 40 and 80 mg simvastatin, respectively, are commercially available. Such a combination medicament has been proven effective in the treatment and/or prevention of atherosclerosis and related conditions.

A pharmaceutical composition comprising ezetimibe and simvastatin is disclosed for example in WO 2004/010993. The composition further includes stabilizing agents/-antioxidative agents such as butylated hydroxyanisole (BHA), 2,6-di-tert-butyl-4-methyl-phenol (BHT), propyl gallate, ascorbic acid, citric acid, edentate disodium and calcium metabisulphite.

Active substances are normally susceptible to environmental influences, such as e.g. storage temperature, humidity, light, (e.g. UV light) and gases, present in the environment, such as oxygen or carbon dioxide. An important factor is also the pH, that is, the presence of substances, which have influence on acidity or alkalinity of the environment (e.g., acids, alkalis, salts, metal oxides) and the reactivity of the ambient medium or active substance (free radicals, heavy metals), etc.

Also excipients contained in pharmaceutical compositions may be a source of impurities and/or oxidants or metals (e.g. present impurities) and may be involved in the occurrence of mobile oxidative species, such as peroxyl-radicals, superoxide (singlet oxygen) and hydroxyl radicals. This depends on the hydrogen bond strength of the excipients and whether there are good electron donor sites (e.g. amines). Peroxide impurities are often present in polymeric excipients and they are a major source of oxidation in pharmaceutical formulations (Waterman, K. C., et al, Stabilization of Pharmaceuticals to Oxidative Degradation, Pharmaceutical Development and Technology, 7(1), 2002, 1-32).

In order to prevent degradation and/or other undesired chemical reactions, such as oxidation reactions, the incorporation of stabilizers/antioxidants is normally ineluctable. Specifically, for preparations containing simvastatin and/or ezetimibe antioxidants are commonly used to stabilize such compositions. Due to their good anti-oxidative properties, BHA and BHT are preferred anti-oxidants used in this respect. Nevertheless, the use of both compounds involves critical shortcomings. BHA is absorbed through the skin, stored in body tissues and has proved to be harmful in higher concentrations. BHT is described as harmful when ingested, inhaled or absorbed through skin. Said compound causes eye and skin irritation and is irritating to mucous membranes and upper respiratory tract. The effects described may vary from mild irritation to severe destruction of tissue. Although current levels of BHA consumption do not appear harmful, further research is warranted to define safe exposure levels (*Food-Chem. Toxicol.*, 24 (10-11), 1986, p. 1163-1166).

Apart from the above shortcomings such protective compounds may also result in the formation of degradation products, which may in turn react with the active substance they were added to preserve in the first place. Degradation products of the latter act as the reactive sites, which trigger degradation reactions of the active substance in a pharmaceutical dosage form.

It is therefore highly desirable to provide chemically stable pharmaceutical compositions for the treatment of atherosclerosis and related conditions or for the reduction of plasma cholesterol levels, which do not show the above shortcomings of the prior art formulations.

The above problem has been solved by providing a pharmaceutical formulation comprising simvastatin and ezetimibe wherein in a first embodiment no stabilizing agents, particularly antioxidants, are included, while according to a second embodiment the contact of the compositions with oxygen is substantially reduced, such as by coating the composition or providing the medicament in an environment having an essentially reduced oxygen or humidity, respectively, content.

It has been found that such compositions exhibit a storage stability, which is even surprisingly improved in comparison to pharmaceutical composition containing the hitherto used antioxidants BHA and BHT. The present pharmaceutical composition provides a high quality finished product with the desirable shelf-life stability.

Without whishing to be bound by any theory, it is presently assumed that the increased stability of the present pharmaceutical composition is just a result of omitting compound(s) with an antioxidative/stabilizing effect, which exerts its preservative activity by scavenging infiltrating oxygen while simultaneously decomposing to unknown degradation products, which in turn may react with chemical reactive groups of the active ingredients simvastatin and ezetimibe again leading to their partial inactivation or to the formation of products detrimental for health. It seems that the degradation products of said antioxidants have catalytic effects on the further degradation/decomposition of the two active compounds, since even traces of said/degradation) products lead to an progressive degradation/decomposition reaction.

It is further believed that particularly BHA and BHT, but also other antioxidants like citric acid or ascorbic acid, may cause an accelerated degradation of the active compounds in a humid environment or a solvated form by acid/base hydrolysis of the respective ester- and lactone-moieties of simvastatin and the lactam-function of ezetimibe or an acid/base induced elimination of the hydroxyalkyl group contained therein.

According to a first embodiment, the present invention relates to pharmaceutical compositions comprising simvastatin and ezetimibe, that do not contain any stabilizing agents, particularly antioxidants.

According to a second embodiment the present invention relates to pharmaceutical compositions wherein the contact thereof with oxygen is substantially reduced, such as by coating the composition or providing the medicament in an environment having an essentially reduced oxygen or humidity, respectively, content.

In a preferred embodiment the present pharmaceutical compositions do not contain stabilizing agents, particularly antioxidants, while at the same time the contact between the pharmaceutical composition, i.e. the active compounds, and oxygen is reduced such that only minimal or no degradation at all of the two active compounds is ensured.

The two active compounds of the present pharmaceutical composition may, if desired, be present in form of a pharmaceutically acceptable salt, which may be prepared for example as alkaline metal or alkaline earth salts, such as sodium, potassium or calcium salts. Organic salts and esters are also suitable for use in this invention.

According to a preferred embodiment, the contact between the pharmaceutical composition and environmental oxygen may be diminished by either packaging the pharmaceutical composition under reduced pressure, packaging in an inert gas atmosphere, using a coating affording protection and stability of the pharmaceutical composition from environmental influences or by using a packaging wherein the contact between the pharmaceutical composition and oxygen is reduced by the means of oxygen absorbers. Producing and packaging the pharmaceutical composition at a reduced partial pressure has on the one hand the effect, that the amount of oxygen and reactive oxygen species is reduced. On the other hand, a reduced water/humidity content and lower amounts of other solvents may be observed, which leads to an additional stabilisation of the active compounds, since hydrolysis mediated degradation/decomposition reactions of simvastatin and ezetimibe do not occur.

An atmosphere with reduced oxygen content or reduced oxygen partial pressure may be obtained by the use of reduced pressure atmosphere, e.g. by creating a partial vacuum by means of a suitable pump or by partial freezing or liquefying the atmosphere, by the use of an inert gas atmosphere, wherein as an inert gas nitrogen or argon may serve for example, or by the use of absorbents. Absorbents may be selected from the group of commercially available absorbents such as humidity-activated oxygen absorbers, ultraviolet-radiation-activated absorbers, radiation-activated absorbers, microwaves-radiation-activated absorbers, absorbers activated by a combination of activation processes or absorbers without necessity of activation. The examples of commercially available absorbers are Ageless™ (Mitsubishi Gas Chemical), ATCO (Standa Industry), FreshPax™ (Multisorb Technologies), O-Buster™ (Hsiao Sung Non-Oxygen Chemical Co), Biotika Oxygen Absorber (Biotika) and the like. The invention also provides a stabilized package of the simvastatin/ezetimibe combination which is provided with a space for trapping and disposal of free oxygen. Moreover, if the active compounds of the present composition are exhibited to a reduced oxygen partial pressure, the formulation is preferably enclosed in a substantially gas exchange non-permeable material and an atmosphere with reduced oxygen partial pressure is contained in the packaging. The substantially gas exchange non-permeable package is preferably selected from the group consisting of an Al/Al blister, an Al-polychloro-3-fluoroethylene homopolymer/PVC laminate blister or a bottle.

In another preferred embodiment, the contact between the pharmaceutical composition and oxygen containing environment is reduced by the use of coatings. Film coatings, which prevent environmental gases to ingress into the cores may be used, for example coatings based on carboxymethylcellulose sodium (NaCMC) or polyvinyl alcohol (PVA), or any other coating known in the state of the art.

The formulations of the present invention may be prepared by well known technological processes such as direct compression or wet granulation (with water or organic solvents), dry granulation or lyophilization. Preferably, a wet granulation process is used, wherein the contact between the pharmaceutical formulation and oxygen is optionally reduced.

In such a wet granulation process, the active compounds in powder form are presented in a suitable granulator and subsequently moistened or sprayed with molten material. The shear forces applied lead to an intensive mixing of the powder and, with the addition of binder solutions, to the rapid formation of high-density granulates. Granulation is required to improve the flow of powder mixtures and mechanical properties of tablets. Granules are usually obtained by adding liquids (binder or solvent solutions). Larger quantities of granulating liquid produce a narrower particle size range and coarser and harder granules, i.e. the proportion of fine granulate particles decreases. The optimal quantity of liquid needed to get a given particle size should be known in order to keep a batch-to-batch variations to a minimum. Wet granulation improves flow, compressibility, bioavailability, homogeneity, electrostatic properties, and stability of solid dosage forms.

According to another embodiment, the present composition is a solid dosage form. Exemplary solid dosage forms of the invention include tablets, capsules, sachets, lozenges, powders, pills or granules. The solid dosage form may be, for example, immediate release dosage form, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred. The solid dosage form is preferably an immediate release dosage form offering advantages regarding the bioavailability of the active compounds.

If an immediate release dosage form is chosen, it will be clear for the skilled person that the amount of release controlling agent(s) to be used in forming the outer portion will be determined based on various parameters such as the desired delivery properties, including the amount of active ingredient or substance to be delivered, the a active ingredient or substance release rate desired, and the size of the micro matrix particles.

The immediate release dosage form may also include a material that improves the processing of the release controlling agents. Such materials are generally referred to as plasticisers. Preferred plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triethyl citrate, triacetin, tripropinoin, diacetin, dibutyl phthalate, acetyl monoglyceride, polyethylene glycols, castor oil, triethyl citrate, polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, dioctyl phthalate, di-i-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate and glyceryl monocaprate.

The dosage form may be manufactured according to the following procedure: The core particles may be produced in accordance with usual techniques in which the active ingredient or substance and one or more release controlling agents are mixed and granulated by adding solvent in a low or high shear mixer or by fluidized bed granulator. The granulate is dried, for example in a fluidized bed dryer. The dried granulate is sized. The sizing of the micromatrix particles may be performed by using an oscillating granulator, comminuting mill or any other conventional method. The sieve used for the sizing may have openings from 0.25 mm to 5 mm. Alternatively the core particles can be made by extrusion, spheronization, melt granulation or by roller compaction. The core particles may be coated by a solution of one or more release controlling agents by any known method, including spray application. Spraying can be carried out using a fluidized bed coater (preferably Wurster coating), or in a pan coating system. Alternatively the coating of the core particles with one or more rate controlling agents can be done by hot melt process using a granulator or fluidized bed coater (preferably Wurster coating), or in a pan coating system. The compression of micro tablets is carried out on usual compression machines (e.g. machines by Manesty, Cadmach or Kilian). The micro tablets can be made of various sizes and shapes like round, oval, oblong, capsule shaped, triangular, square, etc. The preferred shape of the micro tablet is round, biconvex and the preferred diameter of the micro tablet is 1.5 mm to 9.5 mm.

The micro tablets may be coated by a solution of one or more release controlling agents by any known method, including spray application. Spraying can be carried out using a fluidized bed coated (preferably Wurster coating), or in a pan coating system.

Alternatively the coating of the micro tablets with one or more rate controlling agents can be done by hot melt process using a fluidized bed coated (preferably Wurster coating), or in a pan coating system. The micro tablets can be filled in the casing using manually operated, semiautomatic or automatic capsule filling machine.

The present composition may by also present in a particular dosage form for improving the bioavailability of simvastatin and ezetimibe. Particularly ezetimibe has a low water solubility. The term bioavailability describes the rate and extent to which the active ingredient or active moiety is absorbed from a drug product and becomes available at the site of action. The bioavailability of orally ingested drugs is determined by factors, which include the nature of the molecule, its stability, and the formulation administered—and in the patient—such as a reduced intestinal surface area as a result of colic disease or intestinal resection and whether or not the drug is taken with a meal. Factors influencing the bioavailability may include, but are not limited to a poor absorption from the gastrointestinal tract, hepatic first-pass effect and degradation of the drug prior to reaching system circulation.

Ezetimibe can be present in different polymorphic and pseudopolymorphic forms such as ezetimibe form known in the art or for example described in WO 2005/009955 as forms H1, H2, the amorphic form or mixtures thereof. Different particle size fractions can be used. Due to low solubility of ezetimibe, preferable particle size is $d_{90}$ less than 100 μm, more preferably less than 50 μm, most preferably less than 10 μm.

According to another embodiment, the present pharmaceutical composition may contain in addition to simvastatin and ezetimibe one or more diluents, binding agents, disintegrants, lubricants, sweeteners, glidants, flavourings, colouring agents and other excipients, depending on the dosage form desired.

Suitable diluents include pharmaceutically acceptable fillers such as lactose, microcrystalline cellulose, dibasic calcium phosphate, saccharides and/or mixtures of the foregoing. Examples of diluents include microcrystalline cellulose, such as Avicel PH 101® and Avicel® PH 102; lactose such as lactose monohydrate, lactose anhydrous and Pharmatose® DCL 21; dibasic calcium phosphate such as Emcompress®; mannitol, starch, sorbitol, sucrose and glucose. The most preferred are microcrystalline cellulose and lactose.

Binding agents are preferably selected from polyvinylpyrolidone, starch grades (pregelatinized or plain), cellulose derivatives such as hydroxypropylmethylcellulose (HPMC), hydroxypropylcellulose (HPC) and carboxymethylcellulose (CMC) and their salts and gelatine, the most preferred is HPMC.

Suitable disintegrants include croscarmellose sodium, crospovidone, sodium starch glycolate, corn starch, potato starch, maize starch and modified starches calcium silicates, low substituted hydroxypropylcellulose and the like. Most preferred is croscarmellose sodium.

Lubricants are preferably selected from the group consisted of magnesium stearate, magnesium lauryl sulfate and sodium stearyl fumarate, sucrose esters or fatty acid, polyethylene glycol, stearic acid and the like.

Sweeteners are preferably selected from the group consisting of aspartame, saccharin sodium, dipotassium glycyrrhizinate, aspartame, stevia, thaumatin, and the like.

Glidants are preferably selected from the group consisting of silicon dioxide, talc and aluminium silicate.

As flavourings, colouring agents, or opacifying agents and pigments any suitable compound known to the skilled person may be used.

According to another preferred embodiment, the simvastatin and ezetimibe are used for the preparation of a medicament for the prevention and/or treatment of atherosclerosis and related conditions or for the reduction of plasma cholesterol levels. Atherosclerosis is a disease characterized by a progressive narrowing and hardening of the arteries over time. The occurrence of atherosclerosis is preliminary known to take place to certain degree with aging, but other risk factors that accelerate this process have been identified, such as high plasma cholesterol, high blood pressure, smoking, diabetes and genetic disposition for atherosclerotic disease.

The present invention is illustrated by the following examples without limiting it thereto.

EXAMPLES

Methods

Impurities were determined via high performance liquid chromatography (HPLC), using an Inertsil ODS-3 column (250 mm×μ4.0 mm i.d., 5 μm particles). Any other equivalent column with the reverse phase C18 as stationary phase may also be applied. If needed, the flow rate and/or gradient elution can be slightly corrected. Gradient elution using mobile phase A (0.01 M ammonium acetate) and mobile phase B (acetonitrile) is applied. Before use both of them are degassed and filtered over a 0.45 μm filter.

Gradient Elution:

| t (min) | % A | % B |
| --- | --- | --- |
| 0 | 60 | 40 |
| 30 | 40 | 60 |
| 50 | 40 | 60 |

Flow rate: approximately 1.0 ml/min
Detection: UV, 230 nm
Injection volume: 10 μL
Temperature of the column: 25° C.

Reference Example

| Component | Amount/mg |
| --- | --- |
| Simvastatin | 20.00 |
| Ezetimibe | 10.00 |
| Lactose | 126.45 |
| Microcrystalline Cellulose | 30.00 |
| HPMC | 4.00 |
| Croscarmellose Sodium | 6.00 |
| Citric Acid | 0.50 |
| Propyl Gallate | 0.01 |
| BHA | 0.04 |
| Magnesium Stearate | 3.00 |
| Purified Water | Approx. 45* |
| Ethanol | Approx. 15* |

*evaporate during the process

BHA and propyl gallate were dissolved ethanol, citric acid was dissolved in purified water and both solutions were mixed to obtain granulating solution. Simvastatin, ezetimibe, lactose, HPMC, half of the microcrystalline cellulose and half of the croscarmellose sodium were mixed and granulated with the solution described above. The rest of ingredients were added and obtained compression mixture was tableted. Due to low solubility of ezetimibe, the micronized form of ezetimibe is preferably used (for example less than 30 μm, most preferably less than 10 μm). Loss on drying of the free flowing granulate was 0.78%, pH of the suspension of formulation in water (20% m/V; Ph. Eur. 2.2.3) was 6.1.

The tablets were packed in Alu-Alu blisters in normal atmosphere (air) and in reduced oxygen partial pressure atmosphere (approx. 4% v/v oxygen) and stored at 50° C. for 3 months and at 40° C./75% relative humidity for 3 months, respectively.

Example 1

| Component | Amount/mg |
| --- | --- |
| Simvastatin | 20.00 |
| Ezetimibe | 10.00 |
| Lactose | 127.00 |
| Microcrystalline Cellulose | 30.00 |
| HPMC | 4.00 |
| Croscarmellose Sodium | 6.00 |
| Magnesium Stearate | 3.00 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm). Loss on drying of the free flowing granulate was 0.80%. pH of the suspension of formulation in water (20% m/V; Ph. Eur. 2.2.3) was 7.5.

The tablets were packed in Alu-Alu blisters in normal atmosphere (air) and in reduced oxygen partial pressure atmosphere (approx. 4% v/v oxygen) and stored at 50° C. for 3 months and at 40° C./75% relative humidity for 3 months, respectively. Degradation products were determined via high performance liquid chromatography (HPLC).

The results of the stability testing were as follows (Table 1 and Table 2):

TABLE 1

| Impurities after 3 months at 50° C. (in %) | Reference example | Example 1 |
| --- | --- | --- |
| Air | 0.62% | 0.29% |
| Reduced oxygen partial pressure atmosphere (approx. 4% v/v oxygen) | 0.46% | 0.18% |

TABLE 2

| Impurities after 3 months at 40° C./ 75% relative humidity (in %) | Reference example | Example 1 |
| --- | --- | --- |
| Air | 0.42% | 0.10% |
| Reduced oxygen partial pressure atmosphere (approx. 4% v/v oxygen) | 0.42% | 0.09% |

From the results in Table 1 it may clearly be seen that, surprisingly, in normal atmosphere, additional stabilisers provided higher quantities of degradation products, whereas inert atmosphere provided an additional improvement of the quality and shelf life of the product. Further on, this effect is even more pronounced in Table 2. Besides, statins, which are in the form of a cyclic ester (lactone), are sensitive to an alkaline or near neutral medium, where they are transformed to an acid form. Surprisingly, composition of the formulation of a higher pH value and without the presence of stabilizing agents also resulted in a high quality product.

Example 2

| Component | Amount/mg |
| --- | --- |
| Simvastatin | 20.00 |
| Ezetimibe | 10.00 |
| Lactose | 124.00 |
| Microcrystalline Cellulose | 30.00 |
| HPMC | 4.00 |
| Croscarmellose Sodium | 6.00 |
| Stearic acid | 6.00 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 3

ODT (Orally Dispersible Tablets)

| Component | Amount/mg |
| --- | --- |
| Simvastatin | 20.00 |
| Ezetimibe | 10.00 |
| Mannitol | 126.00 |
| Microcrystalline Cellulose | 18.00 |
| Low substituted HPC | 13.50 |
| Aspartame | 1.50 |
| Crospovidone | 18.00 |
| Calcium silicate | 30.00 |
| Magnesium Stearate | 3.00 |
| Purified Water | Approx. 75* |

*evaporates during the process

Simvastatin, ezetimibe, mannitol, microcrystalline cellulose, low substituted hydroxylpropylcellulose, aspartame and crospovidone were granulated with purified water in high shear mixer. The rest of ingredients were added and obtained compression mixture was tableted to obtain fast disintegrating tablets. The hardness of the tablets was 40-50 N and the disintegration time <30 s.

Example 4

| Component | Amount/mg |
| --- | --- |
| Simvastatin | 40.00 |
| Lactose | 276.00 |
| Microcrystalline Cellulose | 60.00 |
| HPMC | 8.00 |
| Croscarmellose Sodium | 12.00 |
| Magnesium Stearate | 4.00 |
| Purified water | Approx. 80* |
| Coating | Amount |
| Opadry White 03H28758 | 10.00 mg |

*evaporates during the process

Simvastatin, lactose, part of microcrystalline cellulose and part of croscarmellose sodium were mixed in a high shear mixer and granulated with HPMC solution in purified water. Granules were dried and sieved and the rest of excipients were added. The obtained mixture was pressed into tablets and coated in coating pan.

Example 5

| Component | Amount/mg |
| --- | --- |
| Ezetimibe | 10.00 |
| Lactose | 55.00 |
| Microcrystalline Cellulose | 20.00 |
| Croscarmellose sodium | 4.00 |
| Sodium laurylsulfate | 2.00 |
| Povidone K25 | 4.00 |
| Magnesium Stearate | 4.00 |
| Purified water | Approx. 10* |

*evaporates during the process

Ezetimibe, lactose, povidone, part of microcrystalline cellulose and part of croscarmellose sodium were mixed in a high shear mixer and granulated with solution of sodium laurylsulfate in purified water. Granules were dried and sieved and the rest of excipients were added. The obtained mixture was pressed into tablets. The mean particle size of ezetimibe was 6 μm and $d_{90}$ 11 μm.

Example 6

ODT

| Component | Amount/mg |
|---|---|
| Ezetimibe | 10.00 |
| Mannitol | 50.00 |
| Microcrystalline Cellulose | 9.00 |
| Low substituted HPC | 7.00 |
| Aspartame | 0.80 |
| Crospovidone | 9.00 |
| Calcium silicate | 15.00 |
| Magnesium Stearate | 1.50 |
| Purified Water | Approx. 35* |

*evaporates during the process

Ezetimibe, mannitol, microcrystalline cellulose, low substituted hydroxylpropylcellulose, aspartame and crospovidone were granulated with purified water in high shear mixer. The rest of ingredients were added and obtained compression mixture was tableted to obtain fast disintegrating tablets. The hardness of the tablets was 40-50 N and the disintegration time <30 s.

Example 7

| Component | Amount/mg |
|---|---|
| Simvastatin | 10.00 |
| Ezetimibe | 10.00 |
| Lactose | 58.50 |
| Microcrystalline Cellulose | 15.00 |
| HPMC | 2.00 |
| Croscarmellose Sodium | 3.00 |
| Magnesium stearate | 1.50 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 8

| Component | Amount/mg |
|---|---|
| Simvastatin | 20.00 |
| Ezetimibe | 10.00 |
| Lactose | 127.00 |
| Microcrystalline Cellulose | 30.00 |
| HPMC | 4.00 |
| Croscarmellose Sodium | 6.00 |
| Magnesium stearate | 3.00 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 9

| Component | Amount/mg |
|---|---|
| Simvastatin | 40.00 |
| Ezetimibe | 10.00 |
| Lactose | 264.00 |
| Microcrystalline Cellulose | 60.00 |
| HPMC | 8.00 |
| Croscarmellose Sodium | 12.00 |
| Magnesium stearate | 6.00 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 10

| Component | Amount/mg |
|---|---|
| Simvastatin | 80.00 |
| Ezetimibe | 10.00 |
| Lactose | 538.04 |
| Microcrystalline Cellulose | 120.00 |
| HPMC | 16.00 |
| Croscarmellose Sodium | 24.00 |
| Magnesium stearate | 12.00 |

Simvastatin, ezetimibe, lactose, HPMC, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 11

| Component | Amount/mg |
|---|---|
| Simvastatin | 10.00 |
| Ezetimibe | 10.00 |
| Lactose | 99.00 |
| Microcrystalline Cellulose | 40.00 |
| Pregelatinized Starch | 20.00 |
| Croscarmellose Sodium | 20.00 |
| Magnesium stearate | 1.00 |

Simvastatin, ezetimibe, lactose, pregelatinized starch, half of the microcrystalline cellulose and half of the croscarmellose sodium were mixed and granulated with the mixture of ethanol/water 1:3. The rest of ingredients were added and obtained compression mixture was tableted. Due to low solubility of ezetimibe, the micronized form of ezetimibe is preferably used (for example less than 30 μm, most preferably less than 10 μm).

Example 12

| Component | Amount/mg |
|---|---|
| Ezetimibe Granulation | |
| Ezetimibe | 10.00 |
| Lactose | 57.50 |
| Microcrystalline Cellulose | 20.00 |
| Povidone | 16.00 |
| Croscarmellose Sodium | 4.00 |
| Simvastatin Granulation | |
| Simvastatin | 10.00 |
| Lactose | 23.75 |
| Microcrystalline Cellulose | 10.00 |
| Povidone | 2.00 |
| Croscarmellose Sodium | 4.00 |
| Lubricant | |
| Magnesium stearate | 0.75 |

Ezetimibe Granulation: Povidone (PVP) was dissolved in a mixture of ethanol/water 1:3. Ezetimibe, lactose, half of the croscarmellose sodium and half of the microcrystalline cellulose in the amounts described above for the ezetimibe granulation were mixed and the resulting mixture was granulated with the povidone solution described above and then blended with the other half of the croscarmellose sodium and microcrystalline cellulose. Due to low solubility of ezetimibe, the micronized form of ezetimibe is preferably used (for example less than 30 μm, most preferably less than 10 μm).

Simvastatin Granulation: Povidone (PVP) was dissolved in a mixture of ethanol/water 1:3. Simvastatin, lactose, half of the croscarmellose sodium and half of the microcrystalline cellulose in the amounts described above for the simvastatin granulation were mixed and the resulting mixture was granulated with the povidone solution described above and then blended with the other half of the croscarmellose sodium and microcrystalline cellulose. Composite Granules: The ezetimibe and simvastatin granules were mixed together, magnesium stearate was added, and the mixture was compressed into tablets.

The invention claimed is:

1. A pharmaceutical composition comprising simvastatin, ezetimibe, and an excipient selected from the group consisting diluents, binding agents, disintegrants, lubricants, sweeteners, glidants, flavourings, colouring agents and combinations thereof, the pharmaceutical composition excluding butylated hydroxyanisole (BHA), 2,6-di-tert-butyl-4-methyl-phenol (BHT), propyl gallate, ascorbic acid, citric acid, edentate disodium and calcium metabisulphite.

2. A pharmaceutical composition according to claim 1, wherein exposure of the pharmaceutical composition to atmospheric oxygen is reduced such that there is minimal degradation of the simvastatin and ezetimibe.

3. The pharmaceutical composition of claim 1, wherein exposure of the pharmaceutical composition to oxygen is reduced by means of providing an atmosphere having reduced oxygen content.

4. The pharmaceutical composition of claim 1, wherein exposure of the pharmaceutical composition to atmospheric oxygen is reduced by means of providing an inert gas atmosphere.

5. The pharmaceutical composition of claim 1, wherein exposure of the pharmaceutical composition to atmospheric oxygen is reduced by means of absorbents.

6. The pharmaceutical composition of claim 1, wherein exposure of the pharmaceutical composition to atmospheric oxygen is reduced by means of a coating of the composition.

7. The pharmaceutical composition of claim 6, wherein the coating is based on carboxymethylcellulose sodium.

8. The pharmaceutical composition of claim 6, wherein the coating is based on polyvinyl alcohol.

9. The pharmaceutical composition according to claim 1, which is in a solid dosage form selected from the group consisting of tablets, capsules, sachets, lozenges, powders, pills and granules.

10. The pharmaceutical composition of claim 1, wherein exposure of the simvastatin and ezetimibe to oxygen is reduced during the preparation of the composition.

11. The pharmaceutical composition of claim 1, wherein exposure of the simvastatin and ezetimibe to oxygen is reduced during the packaging of the composition.

12. A pharmaceutical composition comprising simvastatin, ezetimibe, and an excipient selected from the group consisting diluents, binding agents, disintegrants, lubricants, sweeteners, glidants, flavourings, colouring agents and combinations thereof, the pharmaceutical composition excluding butylated hydroxyanisole (BHA), 2,6-di-tert-butyl-4-methyl-phenol (BHT), propyl gallate, ascorbic acid, citric acid, edentate disodium and calcium metabisulphite.

* * * * *